(12) United States Patent
Wang et al.

(10) Patent No.: US 11,344,719 B2
(45) Date of Patent: May 31, 2022

(54) ELECTRIC BANDAGE FOR ACCELERATED WOUND RECOVERY

(71) Applicant: Wisconsin Alumni Research Foundation, Madison, WI (US)

(72) Inventors: Xudong Wang, Middleton, WI (US); Yin Long, Madison, WI (US); Weibo Cai, Madison, WI (US); Hao Wei, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 516 days.

(21) Appl. No.: 16/376,178

(22) Filed: Apr. 5, 2019

(65) Prior Publication Data

US 2020/0316366 A1 Oct. 8, 2020

(51) Int. Cl.

| A61F 13/00 | (2006.01) |
|---|---|
| A61N 1/04 | (2006.01) |
| H02N 1/04 | (2006.01) |
| H02N 2/18 | (2006.01) |
| A61N 1/20 | (2006.01) |
| A61F 13/02 | (2006.01) |

(52) U.S. Cl.
CPC ...... *A61N 1/0468* (2013.01); *A61F 13/00051* (2013.01); *A61F 13/0253* (2013.01); *A61F 13/0273* (2013.01); *A61N 1/0492* (2013.01); *A61N 1/205* (2013.01); *H02N 1/04* (2013.01); *H02N 2/18* (2013.01); *A61F 2013/0034* (2013.01)

(58) Field of Classification Search
CPC .... A61N 1/205; A61N 1/0468; A61N 1/0464; A61N 1/0492; A61N 1/04; A61N 1/0404; A61N 1/0408; A61N 1/0416; A61N 1/042; A61F 2013/00361; A61F 2013/0034; A61F 2013/00234; A61F 2013/002461; A61F 2013/00051; A61F 13/0253; A61F 13/0273; A61F 13/00051
See application file for complete search history.

(56) References Cited

U.S. PATENT DOCUMENTS

| 2003/0130707 A1 | 7/2003 | Gan et al. | |
|---|---|---|---|
| 2011/0130697 A1* | 6/2011 | Nagle | A61N 1/0468 |
| | | | 602/53 |

(Continued)

FOREIGN PATENT DOCUMENTS

| GB | 2434544 A | * 8/2007 | ........... A61N 1/0468 |
|---|---|---|---|
| WO | WO-2006114997 A1 | * 11/2006 | ............. A61N 1/205 |

OTHER PUBLICATIONS

Bhang et al., "Zinc Oxide Nanorod-Based Piezoelectric Dermal Patch for Wound Healing", Advanced Functional Materials 2017, 27, 1603497, pp. 1-13.

(Continued)

*Primary Examiner* — Kim M Lewis
(74) *Attorney, Agent, or Firm* — Boyle Fredrickson S.C.

(57) ABSTRACT

A wearable medical bandage is provided having an energy harvesting generator that harvests mechanical energy from the user's natural body and muscle motions to produce electrical energy. The electrical energy induces an electric potential across the wound opening producing accelerated skin wound recovery under the voltage fluctuations produced by the power generator.

19 Claims, 4 Drawing Sheets

(56) References Cited

U.S. PATENT DOCUMENTS

| | | | |
|---|---|---|---|
| 2015/0182741 A1* | 7/2015 | Baik | A61L 15/26 |
| | | | 607/152 |
| 2015/0290028 A1* | 10/2015 | Isserow | A61N 5/0616 |
| | | | 607/109 |
| 2015/0376599 A1 | 12/2015 | Subramaniam et al. | |
| 2016/0058998 A1* | 3/2016 | Skiba | A61N 1/326 |
| | | | 607/50 |
| 2018/0085569 A1* | 3/2018 | Aganyan | A61H 39/086 |
| 2018/0338866 A1* | 11/2018 | Kharazmi | A61F 13/00063 |
| 2021/0202748 A1* | 7/2021 | Haick | H01L 29/42384 |

OTHER PUBLICATIONS

Thakral et al., "Electrical Stimulation to Accelerate Wound Healing", Diabetic Food & Ankle 2013, 4: 22081, pp. 1-9.

Rasel et al., "A sandpaper assisted micro-structured polydimethylsiloxane fabrication for human skin based triboelectric energy harvesting application", Applied Energy 206 (2017) pp. 150-158.

* cited by examiner

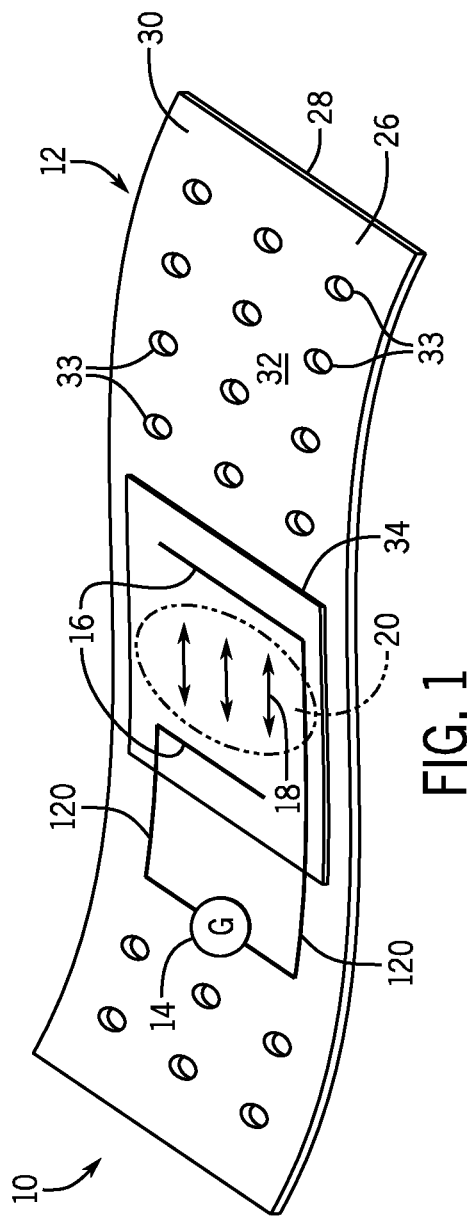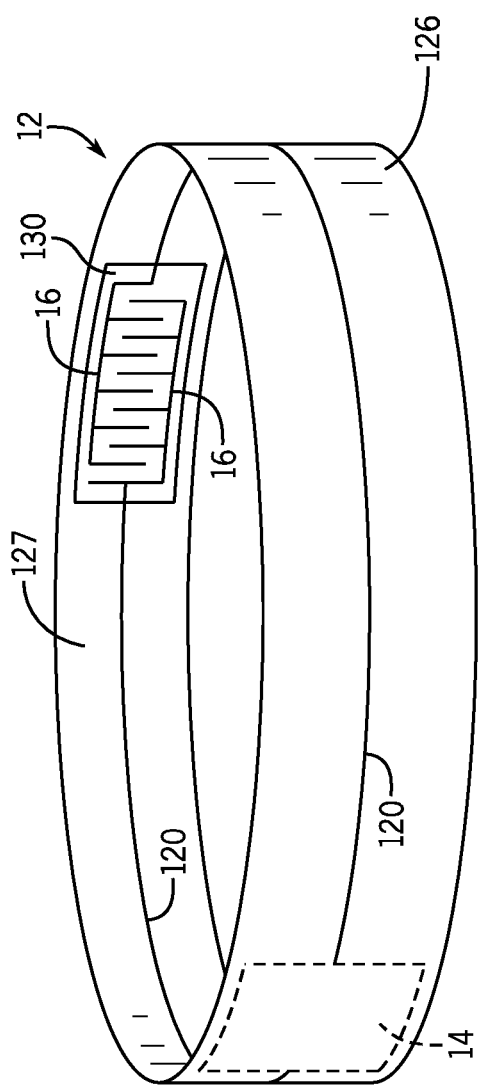

ELECTRIC BANDAGE FOR ACCELERATED WOUND RECOVERY

This invention was made with government support under EB021336 awarded by the National Institutes of Health. The government has certain rights in the invention.

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to a medical bandage for wound recovery, and more particularly, a self-contained electrical energy generating medical bandage to accelerate wound healing.

Non-healing skin wounds, such as diabetic foot ulcers, venous-related ulcerations, and non-healing surgical wounds affect more than 6.5 million people in the United States and result in enormous health care expenditures, with the total cost estimated at more than $25 billion per year. The principal goal in skin wound management is to achieve rapid wound closure and healing.

Owing to the large advancements of modern biomedicine and medical technology, the last several decades have seen the evolution of a number of more effective treatment strategies, including invasive methods such as wound debridement and noninvasive methods such as compression bandaging, wound dressing, hyperbaric oxygen therapy, negative pressure therapy, ultrasound, and electrical stimulation. Most of these methods are external treatments acting on the wound and rarely participate in controlling endogenous cell behaviors.

Currently, advanced growth factor-mediated therapy has emerged as an effective approach for regenerative skin wound healing, which still faces the challenges of rapid degradation and loss of bioactivity. Electrical stimulation for wound healing is an attractive adjunct to wound care. It is believed that electric stimulation directs many cellular processes that lead to orderly, natural healing of wounds. Electrical stimulation can decrease edema around the electrode, lyse or liquefy necrotic tissue, stimulate growth of granulation tissue, increase blood flow, cause fibroblasts to proliferate and make collagen, induce epidermal cell migration, attract neutrophils, stimulate neurite growth directionally, promote epithelial growth and organization, decrease mast cells in healing wounds, attract macrophages, and stimulate receptor sites to accept certain growth factors.

Although the influence from electrical stimulation can be significant, clinical applications of electrical stimulation for wound healing typically involves large-sized extracorporeal devices to provide appropriate amounts of electric current to the skin and may require patient hospitalization.

SUMMARY OF THE INVENTION

The present invention provides a wearable medical bandage having an energy harvesting generator that harvests mechanical energy from the user's natural body and muscle motions to produce electrical energy. The electrical energy induces an electric potential across the wound opening producing accelerated skin wound recovery under the voltage fluctuations produced by the power generator. The present inventors have found that frequent, extended delivery of discrete, alternating electric fields across the wound increases the effectiveness of the electrical stimulation.

In one embodiment, a bandage for wounds on skin is provided having a flexible substrate adapted for retention on the skin at the site of the wound, the flexible substrate having a first surface facing the wound; an electrical generator supported by the substrate to convert mechanical energy harvested from movements of the skin into an electrical potential; and a first and second electrode supported by the substrate in opposition along a plane of the skin and adapted to be positioned over the wound and electrically communicating with the electrical generator for receiving the electrical potential from the electrical generator and applying the electrical potential across the wound.

It is thus a feature of at least one embodiment of the present invention to provide a wearable bandage that is able to produce an electric potential across the wound thus directing cell growth across the wound opening instead of into the wound.

The first and second electrodes may be flexible to conform to a surface of the patient's skin.

It is thus a feature of at least one embodiment of the present invention to allow the electrode placement of the bandage to conform to the wound area for close placement of the electrodes over or in close proximity to the wound.

Flexible conductors may communicate between the first and second electrodes and the power generator displaced from the wound.

It is thus a feature of at least one embodiment of the present invention to harness energy from skin displacements proximate the wound and electrodes and supported on a common substrate.

The power generator may be flexible.

It is thus a feature of at least one embodiment of the present invention to provide a bandage that allows for unrestricted movement of the patient's body when the bandage is being worn to better capture the patient's body movements.

The first and second electrodes may further include interdigitated fingers extending across the wound. A separation between the interdigitated fingers may be less than 10 µm.

It is thus a feature of at least one embodiment of the present invention to provide high gradient electric fields across the wound by decreasing a distance between the electrodes over and across the wound.

The first and second electrode may flank the wound and induce an electric field primarily parallel to a surface of the skin.

It is thus a feature of at least one embodiment of the present invention to encourage high electric field strength across the wound opening rather than into the wound opening.

The first and second electrodes may be parallel line electrodes comprising substantially parallel conductors flanking at least one area of the substrate adapted to be positioned over the wound.

It is thus a feature of at least one embodiment of the present invention to provide a bandage that supports positioning of the electrodes in a flanking configuration over the wound.

An electric potential generated across the first and second electrodes may be at least 0.05 volt. A gradient of an electric field generated between the first and second electrodes may be greater than 100 mV per millimeter.

It is thus a feature of at least one embodiment of the present invention to elicit high gradient electric fields regardless of voltage or frequency using a high density electrode configuration.

An insulator may be placed between the first and second electrodes and the skin to minimize current flow across the first and second electrodes. A current flow across the first and second electrodes may be less than 1 μA amps. The insulator may be polydimethylsiloxane (PDMS).

It is thus a feature of at least one embodiment of the present invention to reduce current flows through healthy tissue to reduce damage to the healthy tissue or adverse effects.

An absorbent pad of material may be placed between the flexible's substrate and the first and second electrode.

It is thus a feature of at least one embodiment of the present invention to facilitate placement of electrodes on the wound by superimposing the electrodes on the absorbent pad where the wound is normally placed against on a medical bandage.

The substrate may be air permeable. An adhesive may be positioned on the first surface of the substrate skin contact surface of the substrate.

It is thus a feature of at least one embodiment of the present invention to allow the energy generator and electrodes to be worn on a medical bandage outside of the hospital environment.

The substrate may be a hoop adapted to elastically fit around a limb of the patient having a wound.

It is thus a feature of at least one embodiment of the present invention to utilize an expanding hoop shaped substrate to capture expansion of the limb causing lateral sliding motions of positive and negative triboelectric materials.

The power generator may include a first and second dielectric material brought into contact with the movements of the skin to elicit an electric potential, i.e. triboelectric generator. In an alternative embodiment, the power generator may be a piezoelectric material, i.e., piezoelectric generator.

It is thus a feature of at least one embodiment of the present invention to harvest mechanical energy from the patient's body without the need for external power supplies.

A method of treating a skin wound may include providing a bandage for wounds on skin having a flexible substrate adapted for retention on the skin at the site of the wound, the flexible substrate having a first surface facing the wound; an electrical generator supported by the substrate to convert mechanical energy harvested from movements of the skin into an electrical potential; and a first and second electrode supported by the substrate in opposition along a plane of the skin and adapted to be positioned over the wound and electrically communicating the electrical power generator for receiving the electrical potential from the generator and applying the electrical potential across the wound. The bandage is attached to the skin wound and worn for at least 24 continuous hours.

These particular objects and advantages may apply to only some embodiments falling within the claims and thus do not define the scope of the invention.

BRIEF DESCRIPTION OF THE DRAWINGS

FIG. 1 is a perspective view of a lower side of a medical bandage of one embodiment of the present invention worn over a skin wound of a human patient and supporting a power generator electrically connected to electrodes producing an electrical field across the wound;

FIG. 2 is a perspective view of an alternative embodiment of the medical bandage of the present invention showing a compression bandage forming a hoop and supporting the power generator and electrodes on the looped bandage facing the skin;

DETAILED DESCRIPTION OF THE PREFERRED EMBODIMENT

Figure 3:
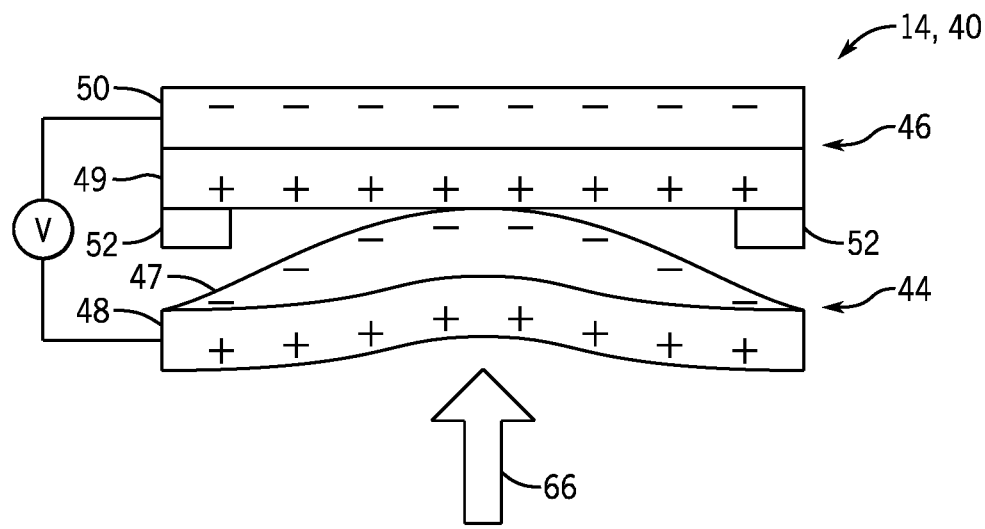
FIG. 3 is a schematic representation of one embodiment of the power generator of FIGS. 1 and 2 showing a triboelectric device generating charge from a vertical contact and separation of oppositely charged dielectric plates.

Referring now to FIG. 1, a wound healing system 10 may be supported on a medical bandage 12 worn by a human patient. An electric energy generator 14 supported by the medical bandage 12 is able to convert the biomechanical (or biochemical) energy into electrical energy that is then used by an electrode pair 16 of the medical bandage 12 to induce an electric potential and electric field 18 across a skin wound 20 of the patient.

The medical bandage 12 may be a small rectangular and flexible sheet of material 26 having a non-adhesive upper side 28 opposite an adhesive wound contact lower side 30 supporting an adhesive 32 to adhere the lower side 30 to the skin of the patient. The flexible sheet of material 26 may be a woven fabric, plastic (PVC, polyethylene or polyurethane), or latex material as is known in the manufacture of medical bandages. The flexible sheet of material 26 may desirably be air permeable with air holes 33, and optionally waterproof yet breathable, for example, having a waterproof membrane with microscopic air holes that allow air to pass through the membrane but are too small for water molecules to pass through. The flexible sheet of material 26 is a biocompatible and non-toxic material to be worn by the human patient.

The adhesive 32 may be a sticky substance such as an acrylate or vinyl resin like methacrylates and epoxy diacrylates, which bond the medical bandage 12 to the patient's skin so that it is not easily detached during normal patient activity and movement but allow it to be removed by peeling the medical bandage 12 off the skin without substantial damage to surface epithelial cells and causing too much discomfort to the patient. The adhesive 32 is also a biocompatible and non-toxic substance to contact the human patient without harm.

A generally rectangular absorbent pad 34 may be generally centered on the lower side 30 of the flexible sheet of material 26 to be desirably placed against the wound 20 without sticking to the wound 20. The absorbent pad 34 may include a thin porous polymer coating to prevent the absorbent pad 34 from sticking to the wound 20. The absorbent pad 34 may be a biocompatible and non-toxic gauze such as cotton, silk or linen which may absorb blood or pus emanating from the wound 20. The absorbent pad 34 may alternatively be a water absorbing hydrogel. The absorbent pad 34 may optionally include an anti-septic solution to disinfect the wound area from disease causing microorganisms and/or an antibiotic solution to treat infections caused by bacteria at the wound area.

An outer surface of the absorbent pad 34 contacting the patient's skin may support the electrode pair 16, communicating with the electric energy generator 14 also supported by the lower side 30 of the flexible sheet of material 26, to facilitate placement of the electrode pair 16 across and substantially parallel to the wound 20 as further described below. The placement of the electrode pair 16 on the outer skin contacting surface of the absorbent pad 34 places the electrodes in close proximity to the wound 20 minimizing electric field decay. It is also understood that the electrode pair 16 may be supported by the adhesive 32 and/or flexible sheet of material 26 without the absorbent pad 34.

The size of the absorbent pad 34 may be generally equal to or greater than the size of the wound 20 to fully cover the wound 20. The skin wound 20 may generally be defined by a cut or break in the skin, or an abrasion to the skin surface which requires epithelial cell recovery over and/or across the skin wound 20. The skin wound 20 generally extends along an upper surface of the skin.

The absorbent pad 34 may have an area as large as 10 cm in length and 10 cm in width for larger wounds and an area as small as 1 cm in length and 1 cm in width for smaller wounds. In this respect the medical bandage 12 is expected to be used on small to medium sized "acute" wounds capable of being substantially covered by the absorbent pad 34 and having a wound area up to 10 cm in length and up to 10 cm in width.

The absorbent pad 34 may be smaller than the flexible sheet of material 26 and surrounded on all sides by the flexible sheet of material 26 and adhesive 32. The flexible sheet of material 26 supporting the absorbent pad 34 may be 20 to 50% larger than the absorbent pad 34 to fully support the absorbent pad 34 and to provide adhesive around the absorbent pad 34 for sticking to the skin. The flexible sheet of material 26 may have an area as large as 15 cm in length and 15 cm in width for larger wounds and an area as small as 2 cm in length and 2 cm in width for smaller wounds.

As is understood in the art, the wound contact lower side 30 of the flexible sheet of material 26 may be covered by a polymer coated paper or plastic sheet prior to use that can be removed by peeling back the polymer coated paper or plastic sheet to reveal the adhesive 32 of the wound contact lower side 30 for application on the skin during use.

Referring now to FIG. 2, an alternative embodiment of the medical bandage 12 may be a compression bandage forming a hoop of material 126 that is flexibly wrapped around a patient's body or patient's limb or extremity, for example, wrapped around the patient's arm, finger, foot, thigh or calf and secured therearound to cover the skin wound 20.

The hoop of material 126 may be a cotton, polyester, latex or elastic yarn material with a desired elasticity allowing the hoop of material to compress against the wound 20. The hoop of material 126 may be a rectangular ribbon or tape having an area up to 15 cm in width corresponding to a width needed to cover a width of the wound 20 and up to 50 cm in length corresponding to an average circumference of a human thigh or up to 150 cm in length corresponding to a largest circumference of the human body desiring to be wrapped such as the chest.

The hoop of material 126 may be fastened and secured in place using aluminum clasps optionally having an elastic portion to clasp an open end of the hoop of material 126 to the hooped material. Alternatively the hoop of material 126 may be formed as a pre-formed hoop sized to elastically fit around the patient's limb or extremity similar to a rubber band. In some embodiments the hoop of material 126 may be a tape having an adhesive on an inner surface 127 that sticks to the skin.

An absorbent pad 130 placed on the inner surface 127 of the hoop of material 112, generally consistent with the absorbent pad 34 of the embodiment shown and described in FIG. 1, may support the pair of electrodes 16 on its inner skin contacting surface in a similar manner as described above. The pair of electrodes 16 may communicate with the electric energy generator 14 also supported by the inner surface 127 of the hoop of material 112.

It is understood that the medical bandage 12 may take other shapes and sizes without deviating from the spirit of the invention. For example, the medical bandage 12 may also be butterfly closures or butterfly stitches for smaller wounds that are applied across the wound 20 in a manner which pulls the skin on the lateral sides of the wound 20 together. In this respect the flexible sheet of material 26 includes opposed adhesive wings flanking the wound 20 and connected by a small non-adhesive bridge spanning the wound 20. The opposed adhesive wings and/or non-adhesive bridge may support the electrode pair 16 to position the electrode pair 16 across the wound 20.

Figure 4:
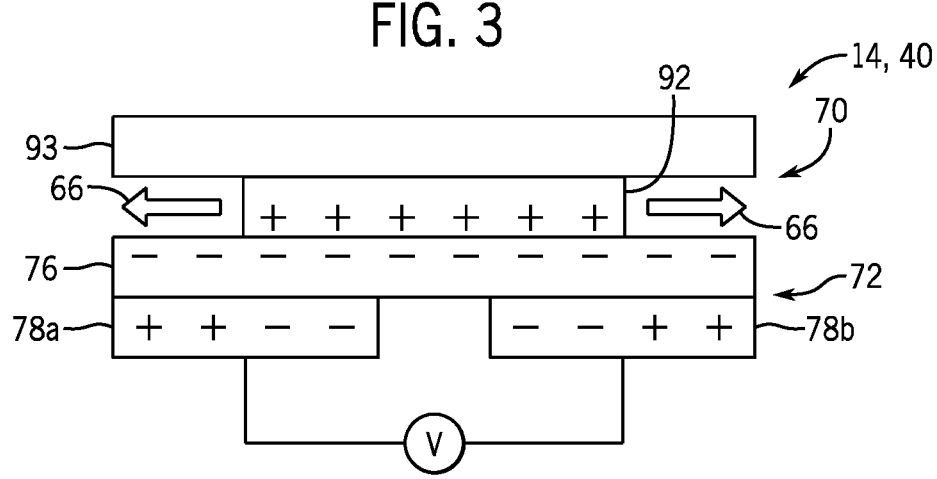
FIG. 4 is a schematic representation of an alternative embodiment of the power generator of FIGS. 1 and 2 showing a triboelectric device generating charge from a lateral sliding of oppositely charged dielectric plates.

Referring also to FIGS. 3 and 4, the energy generator 14 supported by the medical bandage 12 may be a wearable nanogenerator converting mechanical, thermal, or light energy produced by microscale physical changes into an electrical charge inducing an electric potential. The energy generator 14 may be a piezoelectric, triboelectric, hydroelectric, photovoltaic, or thermo-electric generator known in the art. The energy generator 14 may also harvest chemical and electrochemical energy from various human body fluids such as tears, saliva, sweat and the like by using the lactate from these fluids to generate electricity as also known in the art. The energy generator 14 may be "self-generating" in that it produces energy without the need for an external power source such as an alternating current (AC) or direct current (DC) power generator or a pre-charged battery as known in the art.

In one embodiment the energy generator 14 may harvest the movement of the patient's body or muscle motions to produce electrical energy. The movement of the body and muscles may be produced by muscle stretching, breathing, blood pulsing and other voluntary and involuntary body movements of the patient. For example, slight movements of the skin may be captured when the patient inhales and exhales or with blood pulsing.

It is understood that the energy generator 14 is desirably lightweight with a minimized surface area to be easily worn on the patient's skin. An area of the energy generator 14 may have a length less than 2 cm and less than 1 cm and a width less than 2 cm and less than 1 cm. The energy generator 14 may be flexible with a thin profile commonly using soft electronic materials so that it may comply with the body's bending movements. The energy generator 14 may be less than 2 cm and less than 1 cm in thickness. The energy generator 14 may be manufactured of biocompatible material to be non-toxic to the patient when worn.

Referring to FIGS. 3 and 4, in one embodiment of the present invention, the energy generator 14 is a triboelectric nanogenerator 40 used to harvest mechanical energy from the body's movements into electricity to induce an electric potential across the wound 20. Generally, the triboelectric nanogenerator 40 is able to create an electric potential used by the wound healing system 10 by creating surface charges between two dielectric materials that exhibit opposite triboelectric polarity when touched. Once separated, the triboelectric potential between the two dielectric materials induces an electric potential on an external load, i.e., electrode pair 16.

Different modes, models and configurations of the triboelectric nanogenerator 40 may be used in connection with the present invention to produce the electric potential at the external load with certain embodiments described below. The triboelectric nanogenerator 40 is generally able to reach area power densities up to 500 W/m$^2$, volume density up to 490 kW/m$^3$, and a corresponding conversion total energy conversion efficiency of 49% to 85%.

Referring to FIG. 3, a first model of the triboelectric nanogenerator 40 is a vertical contact separation model which is based on switching between contact and separation of two oppositely charged triboelectric materials. In the contact separation model, a lower polymer sheet 44 and an upper polymer sheet 46 are assembled as a sandwiched structure where tribo-positive and tribo-negative dielectric films of the lower polymer sheet 44 and upper polymer sheet 46, respectively, form inner layers of the sandwiched structure that contact and separate with the body's movements.

The lower polymer sheet 44 includes an upper tribo-negative dielectric film 47 of triboelectrically negative dielectric material that will obtain a more negative charge when touched with another material. In one embodiment the tribo-negative dielectric film 47 is a uniform polydimethylsiloxane (PDMS) film. Other materials that exhibit a tribo-negative charge which may be used as the upper dielectric material 47 include polytetrafluoroethylene (PTFE), polyethylene, polypropylene, vinyl (PVC), silicon, silicone rubber, ebonite and the like which are known in the art.

The tribo-negative dielectric film 47 may be patterned to form a uniform array of micro-pyramids. For example, the micro-pyramid pattern may be fabricated by curing the PDMS forming solution on silicon molds by photolithography. Instead of micro-pyramids, it is also understood that micro- or nano-cubes, lines, squares or hemispheres may also be used to enhance the contact area and the electric output. It has been found that the micro-patterns improve the mechanical rigidity and the electrical output of the triboelectric nanogenerator 40. For example, smaller micro-pyramids provide larger contact area and higher electric output.

Deposited on the back side of the tribo-negative dielectric film 47 of the lower polymer sheet 44 is a lower electrode 48 used to produce equal but opposite polarity charges formed by the electrostatic induction of the triboelectric potential generated between the positive and negative dielectric films and to connect the electric potential to the external load. In one embodiment the lower electrode 48 is a thin layer of a metal film such as a gold film. Other conducting materials that may form the lower electrode 48 include indium tin oxide (ITO), aluminum, copper, silver, and the like which are known in the art.

The lower polymer sheet 44 contacts the upper polymer sheet 46 supporting an upper tribo-positive dielectric film 49 of triboelectrically positive dielectric material that will obtain a more positive charge when touched with another material. In one embodiment the tribo-positive dielectric film 49 is a silk film. Other materials that exhibit a tribo-positive charge which may be used as the positive dielectric film 49 include nylon (polyamide), latex, paper, aluminum, cotton, polyester (PET) and the like which are known in the art.

Deposited on the back of the tribo-positive dielectric film 49 is an upper electrode 50. In a similar manner as the lower electrode 48, the upper electrode 50 is used to produce equal but opposite polarity charges formed by the electrostatic induction of the triboelectric potential generated between the positive and negative dielectric films and to connect the electric potential to the external load. In one embodiment the upper electrode 50 is a metal film such as a conductive indium tin oxide (ITO) coated polyethylene terephthalate (PET) film. Other conducting materials suitable for use as the upper electrode 50 include gold, aluminum, copper, silver, and the like which are known in the art.

A spacer 52 may be inserted between the lower polymer sheet 44 and the upper polymer sheet 46 to facilitate the contact and separation of the respective sheets. The spacer 52 may be an elastic material, a foam material, an arch, or a spring, and the like formed by or placed between the lower polymer sheet 44 and upper polymer sheet 46 to provide contact and separation of the lower polymer sheet 44 and the upper polymer sheet 46.

In one embodiment the spacer 52 may be formed of a frame layer at the outer edges of the lower polymer sheet 44 and the upper polymer sheet 46 leaving a cavity at the center between the lower polymer sheet 44 and the upper polymer sheet 46. The frame layer may be an insulating polymer sheet with double sided adhesive adhering to the lower polymer sheet 44 and the upper polymer sheet 46 at their perimeters. In another embodiment, the spacer 52 may be an arch formed by at least one of the lower polymer sheet 44 and the upper polymer sheet 46 where at least one of the lower polymer sheet 44 and the upper polymer sheet 46 is formed to naturally bend outward away from the opposite sheet so that a gap is formed between the lower polymer sheet 44 and the upper polymer sheet 46.

The contact surfaces of the tribo-negative dielectric film 47 and the tribo-positive dielectric film 49 have nanoscale roughness structures which produce friction between the two films 47, 49 thus producing opposite triboelectric charges. When the external force 66 from the body's movements bends the lower polymer sheet 44 upwards, the tribo-negative dielectric film 47 touches the tribo-positive dielectric film 49 to produce opposite charges distributed on the respective contact surfaces of the tribo-negative dielectric film 47 and tribo-positive dielectric film 49. In this respect the tribo-negative dielectric film 47 that possesses a strong electron attracting ability will develop a negative charge and the tribo-positive dielectric film 49 will develop a positive charge.

The triboelectric potential created between the dielectric films 47, 49 induces an opposite charge on the lower electrode 48 and the upper electrode 50 thus creating an electric potential between the lower electrode 48 and upper electrode 50. When the external force 66 is released, the tribo-negative dielectric film 47 and tribo-positive dielectric film 49 separate and the electric potential will neutralize. When the external force 66 is reapplied, the triboelectric potential is created again between the dielectric films 47, 49 inducing an opposite charge on the lower electrode 48 and upper electrode 50. The voltage fluctuations between the lower electrode 48 and upper electrode 50 is induced across electrical conductors to the electrode pair 16 as further described below.

Referring to FIG. 4, a second model of the triboelectric nanogenerator 40 is a lateral sliding model which is based on a "freestanding" polymer sheet 70 sliding along a "stationary" polymer sheet 72 having two fixed conductors 78 deposited on the back of the stationary polymer sheet 72. In the lateral sliding model, the freestanding polymer sheet 70 and stationary polymer sheet 72 include sandwiched layers of tribo-positive and tribo-negative dielectric films which slide with respect to one another with the body's movements. The stationary polymer sheet 72 and the freestanding polymer sheet 70 may be packaged within a silicone elastomer with low friction surfaces that allow for sliding of the layers against each other with minimal resistance.

The stationary polymer sheet 72 may include a thin layer of flexible polyethylene terephthalate (PET) substrate having a tribo-negative dielectric film 76 of triboelectrically negative dielectric material contacting the freestanding polymer sheet 70 and is a material that will obtain a more negative charge when touched with another material. In one embodiment the lower dielectric film 76 is polytetrafluoroethylene (PTFE) but may also be other tribo-negative materials such as polydimethylsiloxane (PDMS), polyethylene, polypropylene, vinyl (PVC), silicon, silicone rubber, ebonite and the like known in the art.

An opposite side of the stationary polymer sheet 72 may support a pair of conductors 78a, 78b for charge collection as the freestanding polymer sheet 70 slides along the stationary polymer sheet 72.

Figures 5, 6:
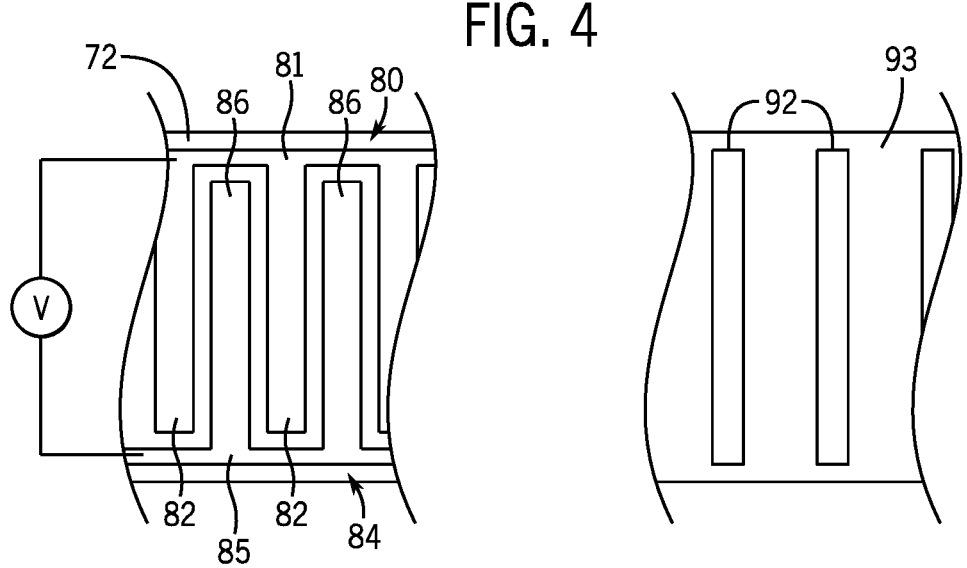
FIG. 5 is a bottom plan view of interdigitated electrodes of a stationary plate of the lateral sliding displacement triboelectric device of FIG. 4.
FIG. 6 is a bottom plan view of strip electrodes of a freestanding plate of the lateral sliding displacement triboelectric device of FIG. 4.

Referring to FIG. 5, in one embodiment, the pair of conductors 78a, 78b are a pair of gold interdigitated electrodes. The pair of gold interdigitated electrodes include a first comb electrode 80 having a longitudinal electrode 81 extending along a length of the stationary polymer sheet 72 and supporting a plurality of conductive fingers 82 arranged perpendicular to the longitudinal electrode 81 extending across a width of the stationary polymer sheet 72. An opposed second comb electrode 84 has a longitudinal electrode 85 extending along the length of the stationary polymer sheet 72 and supporting a plurality of conductive fingers 86 arranged perpendicular to the longitudinal electrode 85 also extending across a width of the stationary polymer sheet 72.

The longitudinal electrode 81 of the first electrode comb 80 and the longitudinal electrode 85 of the second comb electrode 84 extend generally parallel flanking the width of the stationary polymer sheet 72. The plurality of conductive fingers 82 of the first comb electrode 80 extend toward the second comb electrode 84 to interdigitate without touching the plurality of extending conductive fingers 86 of the second comb electrode 84 extending toward the first comb electrode 80 to provide an alternating arrangement of fingers 82, 86 in close lateral alignment along a length of the stationary polymer sheet 72.

The close lateral alignment of fingers 82, 86 allow for short lateral displacements of the freestanding polymer sheet 70 with respect to the stationary polymer sheet 72 to transport charge between the alternating pair of comb electrodes 80, 84. A width of the conductive fingers 82, 84 of the pair of comb electrodes 80, 84 may be between 10 μm to 40 μm and spaced less than 10 μm and less than 5 μm apart to capture microscale lateral displacements. A length of the conductive fingers 82, 84 may be slightly shorter than a width of the stationary polymer sheet 72. The length of the conductive fingers 82, 84 may be 1 cm.

The stationary polymer sheet 72 slides against the freestanding polymer sheet 70, the freestanding polymer sheet 70 having a flexible polyethylene terephthalate (PET) substrate including a tribo-positive dielectric 92 of triboelectrically positive dielectric material that contacts the tribo-negative dielectric film 76 of the stationary polymer sheet 72 and is a material that will obtain a more positive charge when touched with another material. The tribo-positive dielectric 92 is deposited on a support layer 93 of polytetrafluoroethylene (PTFE).

As seen in FIG. 6, in one embodiment the tribo-positive dielectric 92 is an array of gold metal strips 92, each gold metal strip extending across a width of the freestanding polymer sheet 70. Each of the gold metal strips 92 may be separated by a gap approximately equal to a width of the conductive fingers 82, 86. For example, the gold metal strips 92 may be separated by a gap between 10 μm to 40 μm. In this respect, the microscale gap between the gold metal strips 92 shortens the charge transport time between the conductors 78a, 78b resulting in higher electric potential with the same displacement and velocity. A width of each gold metal strips 92 may be between 10 μm to 40 μm. A length of each gold metal strip 92 may be approximately equal to the length of the conductive fingers 82, 86.

The contact surfaces of the tribo-negative dielectric 76 of the stationary polymer sheet 72 and the tribo-positive dielectric 92 of the freestanding polymer sheet 70 have nanoscale roughness structures which produce friction between the two dielectric materials 76, 92 producing opposite charges. When the external force 66 from the body's movements slides the freestanding polymer sheet 70 along the stationary polymer sheet 72, opposite charges are distributed on the contact surfaces of the tribo-negative dielectric 76 and tribo-positive dielectric 92. In this respect the tribo-negative dielectric 76 that possesses a strong electron attracting ability will develop a negative charge and the tribo-positive dielectric 92 will develop a positive charge. Since the negative charge on the tribo-negative dielectric 76 and the positive charge on the tribo-positive dielectric 92 remain constant as the stationary polymer sheet 72 and freestanding polymer sheet 70 slide along each other, the driving force of the current is induced by the sliding of the tribo-positive dielectric 92 with respect to the pair of conductors 78a, 78b, inducing an opposite charge on the pair of conductors 78a, 78b as it moves between the pair of conductors 78a, 78b thus creating an electric potential between the pair of comb conductors 80, 86. The voltage fluctuations between the comb conductors 80, 84 is induced across electrical conductors to the electrode pair 16 as further described below.

It is understood that other modes and arrangements of the triboelectric nanogenerator 40 may be used in connection with the present invention. For example, various types of vertical contact separation mode, lateral sliding mode, and single electrode mode may be used in connection with the present invention.

Although a triboelectric nanogenerator 40 is described above it is also understood that other types of wearable nanogenerators may also be used in connection with the present invention, for example, a piezoelectric nanogenerator may be used utilizing a nano-structured piezoelectric material or piezoelectric thin film such that when an external force is applied an electric field is produced across the piezoelectric material which can induce an electric potential across electrical connectors to the electrode pair 16 as known in the art.

Referring again to FIG. 2, in one embodiment of the present invention the hoop of material 126 of medical bandage 12 is wrapped around the patient's body or limb such that the energy generator 14 is supported by the hoop of material 126 on the inner surface 127 and is thus positioned to be sensitive to skin displacements to harvest the body's movements. It is understood, however, that the energy generator 14 may be supported on the inner, outer, or interior of the medical bandage 12 material. When the energy generator 14 is a triboelectric nanogenerator 40 implementing the contact separation model, for example as described above with respect to FIG. 3, it may be desired that the entire hoop of material 126 will have a uniformly constant ultralow elasticity so that the pulse induced vertical skin displacement will be concentrated at the triboelectric nanogenerator 40 which is the most elastic area of the hoop of material 126. When the energy generator 14 is a triboelectric nanogenerator 40 implementing the lateral sliding model, for example as described above with respect to FIG. 4, it may be desired that only the area surrounding the triboelectric nanogenerator 40 is a highly elastic fabric and the remaining material of the hoop be inelastic to ensure that all expansion displacements are concentrated at the triboelectric nanogenerator 40.

Figure 8:
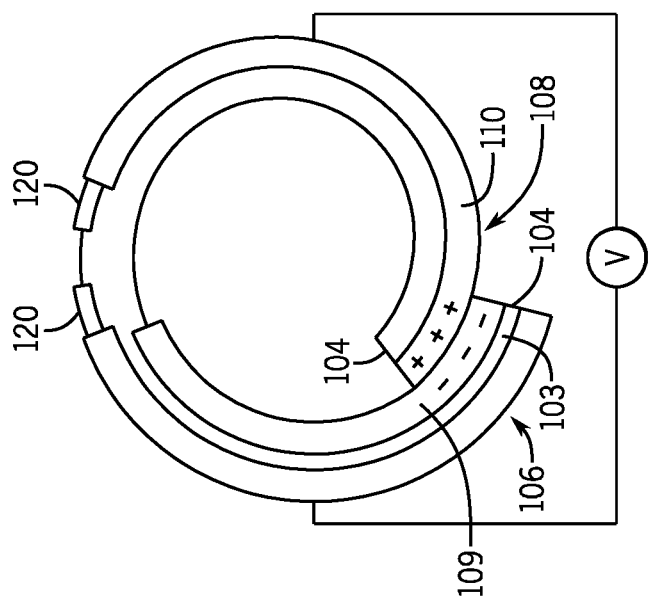
FIG. 8 is a schematic representation of the compression bandage of FIG. 2 as the human patient inhales and the bandage is expanded.
Figure 7:
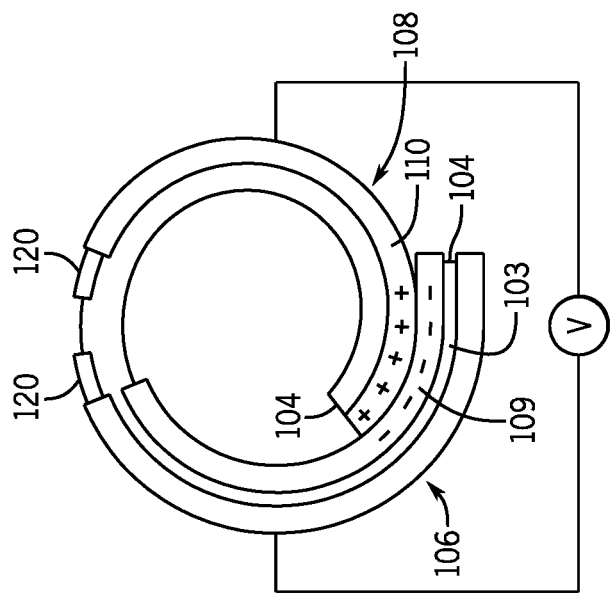
FIG. 7 is a schematic representation of the compression bandage of FIG. 2 as the human patient exhales and the bandage is compressed.

Referring to FIGS. 7 and 8, in one embodiment of the present invention, the triboelectric nanogenerator 40 implementing the lateral sliding model may comprise of a substrate material 103, for example, a polyethylene terephthalate (PET) substrate forming a hoop having outer ends 104 carrying the triboelectric nanogenerator 40. In this respect the outer ends 104 may include an outer polymer sheet 106 (carrying the tribo-negative material) sliding along an inner polymer sheet 108 (carrying the tribo-positive material).

The outer polymer sheet 106 may support a tribo-negative dielectric film 109 of triboelectrically negative dielectric material that contacts the inner polymer sheet 108. The tribo-negative dielectric film 109 may be polytetrafluoroethylene (PTFE). The dielectric material of the outer polymer sheet 106 is selected to have good flexibility, for example, PTFE has a Young's modulus of 0.5 GPa allowing the outer polymer sheet 106 to slide back and forth relative to the inner polymer sheet 108 with relative ease.

The inner polymer sheet 108 may support a tribo-positive dielectric film 110 of triboelectrically positive dielectric material that contacts the outer polymer sheet 106. The tribo-positive dielectric film 110 may be a copper film.

As seen in FIG. 7, when the body is compressed, for example, during exhalation, the inner polymer sheet 108 slides along the outer polymer sheet 106 to overlap and induce negative and positive charges on the tribo-negative dielectric film 109 and the tribo-positive dielectric film 110, respectively.

As seen in FIG. 8, when the body is expanded, for example, during inhalation, the inner polymer sheet 108 slide away from the outer polymer sheet 106 to reduce the overlap and induce negative and positive charges on the tribo-negative dielectric film 109 and the tribo-positive dielectric film 110, respectively.

Referring also to FIG. 2, the voltage fluctuations between the inner polymer sheet 108 and outer polymer sheet 106 created by the movement of the tribo-positive dielectric film 110 along the tribo-negative dielectric film 109 is induced along electrically conductive wires 120 extending between the energy generator 14 and the electrode pair 16 on an opposite end of the triboelectric nanogenerator 40. For example, the electrically conductive wires 120 may flexibly extend from the energy generator 14 in opposite directions along the hoop of material 126 to the pair of electrodes 16. The electrically conductive wires 120 may be insulated conducting wires, for example, copper wires insulated with polydimethylsiloxane (PDMS) to prevent charge from flowing to the surrounding tissue being dissipated in surrounding tissue or exposing the tissue to chemical reactions. The ends of the electrically conductive wires 120 may terminate at the pair of electrodes 16.

The pair of electrodes 16 may be positioned along the hoop of material 126, for example, positioned on an opposite end of the hoop of material 126 from the energy generator 14. In this respect, the energy generator 14 may harvest skin motions displaced from the wound 20 where there is greater likelihood of healthy tissue and normal skin movement. However, it is understood that the pair of electrodes 16 may be positioned at any position along the hoop of material 126 with respect to the location of the energy generator 14. For example, in some embodiments, the pair of electrodes 16 and the energy generator may be positioned in close proximity along the hoop of material 126 to reduce the length of at least one of the conductive wires 120. This is similar to the embodiment shown in FIG. 1 where the conductive wires 120 extend only a short distance on the flexible sheet of material 26 between the energy generator 14 and the pair of electrodes 16.

Referring also to FIG. 1, the absorbent pad 130 on the flexible sheet of material 26 or hoop of material 126 may visually indicate a desired placement of the pair of electrodes 16 with respect to the wound 20 and to encourage placement of the electrodes 16 across the wound 20. In this respect it is desired that the pair of electrodes 16 be positioned so that the electrodes flank the wound 20 to provide an electric potential across the wound 20. The fluctuating electric potential across the wound 20 induces discrete electric fields 18 extending across and substantially parallel to the skin wound 20, in contrast to an electric field extending perpendicular or downward into the wound 20.

The pair of electrodes 16 may be parallel line electrodes, shown in FIG. 1, extending along opposite side ends of the absorbent pad 130 flanking a width of the absorbent pad 130 and therefore desirably flanking the skin wound 20 to generate the electric field 18 across the pair of electrodes 16. The pair of electrodes 16 may be different types of electrodes known in the art and able to produce the electric field across the wound 20. It is understood that the pair of electrodes 16 may also flank a length of the absorbent pad 130 in a similar manner.

Figure 9:
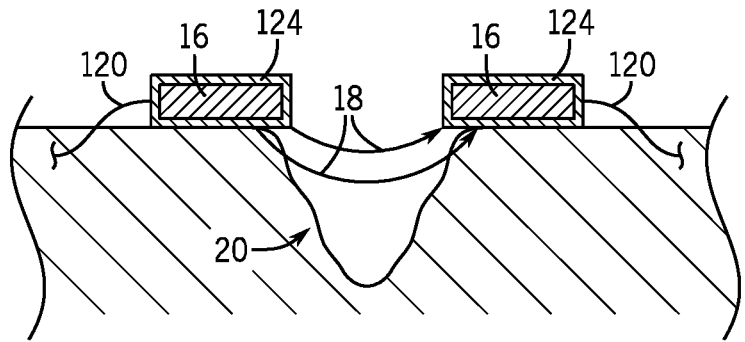
FIG. 9 is a cross-section of the skin wound showing the electric field extending across the electrodes primarily across the wound.

Referring also to FIG. 9, the pair of electrodes 16 may be gold electrodes manufactured using electric beam deposition on a thin polydimethylsiloxane (PDMS) substrate and covered by a thin outer layer 124, for example, another layer of PDMS. The outer layer 124 may be a hydrophobic material able to prevent undesired shortage if blood or other liquids were to be encountered by the pair of electrodes 16. The outer layer 124 may also be an insulator to minimize current flow across the pair of electrodes 16 and between the electrodes and the skin that may injure the surrounding tissue or organs and create reactive oxygen species (ROS) which are harmful to the biological system and may cause damage or even death to cell structures. For example, the minimized current flow between the pair of electrodes 16 may be less than 1 µA.

The electric field 18 strength outside the area between the pair of electrodes 16, along a plane of the wound 20, is close to negligible having minimal impact to the surrounding tissue or organs. Moreover, the electric field 18 strength above or below the pair of electrodes 16, in a direction perpendicular to the wound 20, is also close to negligible having minimal impact to tissue or organs above or below the skin wound 20. In this respect the electric field 18 is directed primarily across the skin wound 20 along a plane of the wound 20.

Figure 10:
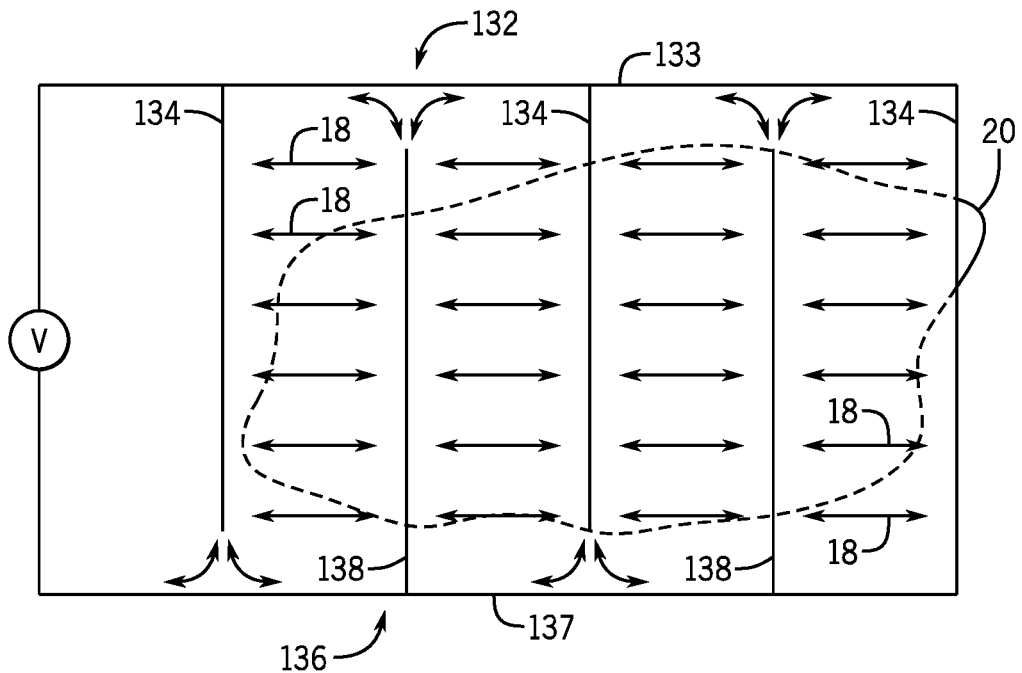
FIG. 10 is a simplified representation of an alternative embodiment of the electrodes of FIG. 1 constructed as a pair of interdigitated electrodes used to produce multiple high intensity electric fields across the wound at shorter distances.

Referring to FIG. 10, in an alternative embodiment, the pair of electrodes 16 may take the form of a pair of interdigitated electrodes. The interdigitated electrodes may be formed of gold, silver, copper, zinc, carbon nanotubes, and any other conducting material known in the art. The pair of interdigitated electrodes provide a first comb electrode 132 having a longitudinal electrode strip 133 extending parallel to a length of the wound 20 and supporting a plurality of conductive fingers 134 extending perpendicular to the longitudinal electrode strip 133 to extend across a width of the wound 20. A second comb electrode 136 has a longitudinal electrode strip 137 extending parallel to the longitudinal electrode strip 133 to flank the wound 20 and supporting a plurality of conductive fingers 138 also arranged to extend across a width of the wound 20.

The longitudinal electrode strip 133 of the first comb electrode 132 and the longitudinal electrode strip 137 of the second comb electrode 136 generally flank the width of the wound 20. The plurality of conductive fingers 134 of the first comb electrode 132 extend toward the second comb electrode 136 across the wound 20 to interdigitated without touching the plurality of conductive fingers 138 of the second comb electrode 136 extending across the wound 20 toward the first comb electrode 132 to provide an alternating arrangement of fingers 134, 138 in close lateral alignment across the wound 20. The lateral spacing between the fingers 134, 138 may be less than 10 mm, and less than 5 mm, and less than 1 mm, and less than 100 μm, and less than 10 μm and less than 5 μm, and may depend on the amplitude of the voltage across the electrodes 132, 136.

The conductive fingers 134, 138 create multiple smaller electric fields 18 spanning across the length of wound 20. The close lateral spacing between the respective conductive fingers 134, 138 of the first and second comb electrode 132, 136, respectively, generally improves the gradient of the smaller electric fields 18 across the wound compared to the single electric field 18 created across the parallel line electrodes of FIG. 1. The gradient is improved by reducing the distances between the conductive fingers 134, 128 of the respective electrodes.

The spacing between the respective fingers 134, 138 may be adjusted to provide a desired electric field 18 strength across the wound 20 under a given electric potential. For example, the gradient of the electric field 18 may be increased by decreasing the distance between the respective fingers 134, 138 for a given electric potential, and the electric field 18 may be decreased by increasing the distance between the respective fingers 134, 138 for a given electric potential.

In using the medical bandage 12, the human patient may remove the paper or plastic backing from the adhesive 32 to expose the adhesive 32 and thereafter place the flexible sheet of material 26 over the wound 20 area, or alternatively wrap the hoop of material 126 around the patient, so that the absorbent pad 34 is placed over the wound 20. The medical bandage 12 is secured to the wound by the adhesive 32, or alternatively by securing the hoop of material 126 around the patient's body by clips or its naturally elastic material. The absorbent pad 34 is placed over the wound 20 to further position the pair of electrodes 16 over the wound 20 so that the electrodes flank the wound 20 opening. In this respect the electrodes 16 may induce the electric field 18 across the wound 20 as produced by the electric generator 14 described above.

The human patient may wear the medical bandage 12 over the wound 20 for an extended period of time, for example, continually for at least 24 hours and between one to three days while participating in normal level activity. The consistent delivery of electric field 18 is in contrast to periodic treatments that may occur for example if the patient is admitted into the hospital for daily electric stimulation treatments.

Based on the patient's normal level activity an average electric potential of at least 0.05 volt and at least 0.1 volts and at least 1 volt may be produced across the pair of electrodes 16. The discrete electric field 18 across the wound 20 may reach a gradient of 10 mV to 3 V per millimeter and at least 10 mV per millimeter, and at least 100 mV per millimeter and at least 1 V per millimeter providing a broad range of electric field strength depending on the electrode design.

Once the treatment is complete, the patient may dispose of the medical bandage 12. It is contemplated that the medical bandage 12 may be used for one time use and then disposed of so as to provide sterility to the treatment method.

Normal level activity may produce various levels of body and skin movements. For example, during respiration, the motions of the thorax and abdomen could lead to 7 to 17 mm radial expansion of the chest wall and even larger expansion of the abdominal wall. Regular heart beating can also create displacement of the chest wall of about 0.45-0.57 mm over the apex and the left ventricle. Blood circulation related skin motions can be sensed over the entire body for example the corroded artery produces a skin displacement of 0.06 mm, the jugular vein produces a skin displacement of 0.01 mm, the radial artery produces a skin displacement of 0.03 mm, and the finger pulse produces a skin displacement of 0.01 mm. Heartbeats can cause a pressure oscillation waves on the body surfaces of the extremities of about 0.26 kPa.

It is understood that although particular embodiments and combinations of the medical bandage 12, electric energy generator 14, and electrode pair 16 are shown and described above, it is understood that any combination of the medical bandage 12, electric energy generator 14, and electrode pair 16 may be used with respect to the wound healing system 10 of the present invention.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A bandage for wounds on skin comprising:
   a flexible substrate adapted for retention on the skin at a site of the wound, the substrate having a first surface facing the wound;
   an electrical generator supported by the substrate to convert mechanical energy harvested from movements of the skin into an electrical potential; and
   a first and second electrode supported by the substrate in opposition along a plane of the skin and adapted to be positioned over the wound and electrically communicating with the electrical generator for receiving the electrical potential from the electrical generator and applying the electrical potential across the wound
   wherein the electrical generator comprises a first and second dielectric material brought into contact with the movements of the skin to elicit an electric potential.

2. The bandage of claim 1 wherein the first and second electrodes are flexible to conform to a surface of the skin.

3. The bandage of claim 1 further including flexible conductors communicating between the first and second electrodes and the electrical generator displaced from the wound.

4. The bandage of claim 1 wherein the electrical generator is flexible.

5. The bandage of claim 1 wherein the first and second electrodes further include interdigitated fingers extending across the wound.

6. The bandage of claim 5 wherein a separation between the interdigitated fingers is less than 1 cm.

7. The bandage of claim 1 wherein the first and second electrodes flank the wound and induce an electric field primarily parallel to a surface of the skin.

8. The bandage of claim 1 wherein the first and second electrodes are parallel line electrodes comprising substantially parallel conductors flanking at least one area of the substrate adapted to be positioned over the wound.

9. The bandage of claim 1 wherein an electric potential generated across the first and second electrodes is at least 0.05 volt.

10. The bandage of claim 1 wherein a gradient of an electric field generated between the first and second electrodes is greater than 10 mV per millimeter.

11. The bandage of claim 1 wherein the substrate is air permeable.

12. The bandage of claim 1 further including an adhesive positioned on the first surface of the substrate facing the wound.

13. The bandage of claim 1 wherein the electrical generator is comprises a piezoelectric material.

14. A bandage for wounds on skin comprising:
    a flexible substrate adapted for retention on the skin at a site of the wound, the substrate having a first surface facing the wound;
    an electrical generator supported by the substrate to convert mechanical energy harvested from movements of the skin into an electrical potential;
    a first and second electrode supported by the substrate in opposition along a plane of the skin and adapted to be positioned over the wound and electrically communicating with the electrical generator for receiving the electrical potential from the electrical generator and applying the electrical potential across the wound; and
    an insulator placed between the first and second electrodes and the skin to minimize current flow across the first and second electrodes.

15. The bandage of claim 14 wherein a current flow across the first and second electrodes is less than 1μA.

16. The bandage of claim 14 wherein the insulator is polydimethylsiloxane (PDMS).

17. A bandage for wounds on skin comprising:
    a flexible substrate adapted for retention on the skin at a site of the wound, the substrate having a first surface facing the wound;
    an electrical generator supported by the substrate to convert mechanical energy harvested from movements of the skin into an electrical potential;
    a first and second electrode supported by the substrate in opposition along a plane of the skin and adapted to be positioned over the wound and electrically communicating with the electrical generator for receiving the electrical potential from the electrical generator and applying the electrical potential across the wound; and
    an absorbent pad of material placed between the substrate and the first and second electrode.

18. A bandage for wounds on skin comprising:
    a flexible substrate adapted for retention on the skin at a site of the wound, the substrate having a first surface facing the wound;
    an electrical generator supported by the substrate to convert mechanical energy harvested from movements of the skin into an electrical potential;
    a first and second electrode supported by the substrate in opposition along a plane of the skin and adapted to be positioned over the wound and electrically communicating with the electrical generator for receiving the electrical potential from the electrical generator and applying the electrical potential across the wound; and
    wherein the substrate is a hoop adapted to elastically fit around a limb of a patient having a wound.

19. A method of treating a skin wound comprising:
providing a bandage for wounds on skin having a flexible substrate adapted for retention on the skin at a site of the wound, the substrate having a first surface facing the wound; an electrical generator supported by the substrate to convert mechanical energy harvested from movements of the skin into an electrical potential; and a first and second electrode supported by the substrate in opposition along a plane of the skin and adapted to be positioned over the wound and electrically communicating the electrical power generator for receiving the electrical potential from the generator and applying the electrical potential across the wound wherein the electrical generator comprises a first and second dielectric material brought into contact with the movements of the skin to elicit an electric potential;
attaching the bandage to the skin wound; and
wearing the bandage on the skin wound for at least 24 continuous hours.

* * * * *